United States Patent
Conroy et al.

(10) Patent No.: US 10,929,774 B2
(45) Date of Patent: Feb. 23, 2021

(54) ROBUST CLASSIFIER

(71) Applicant: KONINKLIJKE PHILIPS N.V., Eindhoven (NL)

(72) Inventors: Bryan Conroy, Garden City South, NY (US); Larry James Eshelman, Ossining, NY (US); Cristhian Potes, Salem, NH (US); Minnan Xu, Cambridge, MA (US)

(73) Assignee: Koninklijke Philips N.V., Eindhoven (NL)

( * ) Notice: Subject to any disclaimer, the term of this patent is extended or adjusted under 35 U.S.C. 154(b) by 779 days.

(21) Appl. No.: 15/549,714

(22) PCT Filed: Feb. 5, 2016

(86) PCT No.: PCT/IB2016/050592
§ 371 (c)(1),
(2) Date: Aug. 9, 2017

(87) PCT Pub. No.: WO2016/128866
PCT Pub. Date: Sep. 18, 2016

(65) Prior Publication Data
US 2018/0046942 A1 Feb. 15, 2018

Related U.S. Application Data

(60) Provisional application No. 62/115,330, filed on Feb. 12, 2015.

(51) Int. Cl.
*G06N 20/00* (2019.01)
*G16H 50/20* (2018.01)
(Continued)

(52) U.S. Cl.
CPC ......... *G06N 20/00* (2019.01); *A61B 5/02028* (2013.01); *A61B 5/7267* (2013.01);
(Continued)

(58) Field of Classification Search
USPC .......................................... 706/12
See application file for complete search history.

(56) References Cited

U.S. PATENT DOCUMENTS 5,175,796 A * 12/1992 Refregier ............. G06K 9/6278
706/20
7,650,321 B2    1/2010 Krishnan et al.
(Continued)

FOREIGN PATENT DOCUMENTS

CN    101777125 A    7/2010
CN    102750286 A    10/2012
(Continued)

OTHER PUBLICATIONS

Smeraldi, et al., "Handling Missing Features with Boosting Algorithms for Protein-Protein Interaction Prediction", Aug. 25, 2010, Data Integration in the Life Sciences (DILS), LNBI 6254, pp. 132-136, 144.

(Continued)

*Primary Examiner* — Michael B Holmes (57) ABSTRACT

Various embodiments described herein relate to methods and apparatus for robust classification. Many real-world datasets suffer from missing or incomplete data. By assigning weights to certain features of a dataset based on which feature(s) are missing or incomplete, embodiments of the prevention can provide robustness and resilience to missing data.

20 Claims, 5 Drawing Sheets

(51) Int. Cl.
*G06F 16/28* (2019.01)
*A61B 5/00* (2006.01)
*G06N 5/04* (2006.01)
*G06F 17/18* (2006.01)
*A61B 5/02* (2006.01)
*G06F 7/08* (2006.01)

(52) U.S. Cl.
CPC .............. *A61B 5/7275* (2013.01); *G06F 7/08* (2013.01); *G06F 16/285* (2019.01); *G06F 17/18* (2013.01); *G06N 5/04* (2013.01); *G16H 50/20* (2018.01); *A61B 2505/03* (2013.01)

(56) References Cited

U.S. PATENT DOCUMENTS

| | | | | |
|---|---|---|---|---|
| 9,141,622 | B1* | 9/2015 | Moore | G06F 16/11 |
| 9,389,431 | B2* | 7/2016 | Wall, III | A61H 3/061 |
| 9,433,348 | B2* | 9/2016 | Eshelman | A61B 5/0002 |
| 9,959,390 | B2* | 5/2018 | Vairavan | G06N 7/005 |
| 10,456,087 | B2* | 10/2019 | Yang | A61B 5/7221 |
| 10,531,801 | B2* | 1/2020 | Cheng | A61B 5/0444 |
| 10,571,715 | B2* | 2/2020 | Rizzo, III | G02C 11/10 |
| 2004/0193036 | A1 | 9/2004 | Comaniciu et al. | |
| 2006/0062451 | A1 | 3/2006 | Li et al. | |
| 2006/0120609 | A1 | 6/2006 | Ivanov et al. | |
| 2006/0184475 | A1 | 8/2006 | Rao et al. | |
| 2015/0023606 | A1* | 1/2015 | Morishita | G06K 9/00255 382/219 |
| 2018/0046942 | A1* | 2/2018 | Conroy | G16H 50/20 |

FOREIGN PATENT DOCUMENTS

| | | |
|---|---|---|
| CN | 102819745 A | 12/2012 |
| CN | 102955946 A | 3/2013 |
| CN | 104035779 A | 9/2014 |
| JP | 2007025978 A | 2/2007 |
| JP | 2013125482 A | 6/2013 |
| WO | 2006088983 A2 | 8/2006 |
| WO | 201131052 A2 | 3/2011 |

OTHER PUBLICATIONS

Sill, et al., "Feature-Weighted Linear Stacking", Nov. 3, 2009, Arxiv.0rg, Cornell University Library.

Conroy, et al., A dynamic ensemble approach to robust classification in the presence of missing data, Machine Learning, vol. 102, No. 3, Oct. 20, 2015, pp. 443-463.

Garcia-Laencina, et al., "Pattern classification with missing data: a review", Neural Computing and Applications, vol. 19, No. 2, Sep. 3, 2009, pp. 263-282.

* cited by examiner

FIG. 6

ROBUST CLASSIFIER

CROSS-REFERENCE TO RELATED APPLICATIONS

This application is the U.S. National Phase application under 35 U.S.C. § 371 of International Application No. PCT/IB2016/050592, filed on Feb. 5, 2016, which claims the benefit of U.S. Provisional Application Ser. No. 62/115,330, filed Feb. 12, 2015. These applications are hereby incorporated by reference herein, for all purposes.

TECHNICAL FIELD

Various embodiments described here generally relate to methods and apparatuses for robust classification, and more particularly, but not exclusively, to classification using datasets that may have missing or incomplete data.

BACKGROUND

Datasets often suffer from missing or incomplete data. Data may be missing from a particular dataset for a variety of reasons, such as insufficient monitoring due to human error or malfunctioning data-acquiring devices. Conclusions or classifications based on such datasets may therefore be inaccurate, regardless of the reason for the missing or incomplete data.

However, there have been certain techniques for handling missing or incomplete data. One technique is referred to as data imputation. Data imputation involves calculating approximations for the missing data. This technique may involve constructing an estimator for missing values for a given data feature. The estimated values may be derived from the other values in the dataset. For example, the estimated values may be, e.g., the population mean, median, mode, or the like.

Data imputation is simple to implement but is not very accurate and may simply inject noise into the data. Additionally, value estimations more complicated than the computation of the mean or median of a data set may require prior knowledge about the relationships between features and/or sophisticated estimation techniques in order to be effective.

Another technique for handling missing or incomplete data is to first build a large collection of classifiers, each of which depends on a different subset of features. Then, the most appropriate classifier is identified based on the pattern of measured features in the present input and evaluated to make a prediction of the missing entries in the overall input pattern.

While this technique avoids the problems of data imputation discussed above, it suffers from its own drawbacks. For one, the number of possible subsets of features is combinatorial in the total number of features. Additionally, storing classifiers on all possible feature subsets (or even a fraction thereof) quickly becomes infeasible as the number of total features increases.

A need exists, therefore, for methods and apparatus for handling data sets with missing or incomplete data that overcomes the above-mentioned disadvantages.

SUMMARY

This summary is provided to introduce a selection of concepts in a simplified form that are further described below in the Detailed Description section. This summary is not intended to identify key features or essential features of the claimed subject matter, nor is it intended to be used as an aid in determining the scope of the claimed subject matter.

Various embodiments relate to an apparatus for robust classification. The apparatus includes a receiver receiving data, the received data having at least one feature from a feature set; a memory configured to store computer-readable instructions for performing robust classification; and a processor in communication with the memory and receiver, wherein execution of the computer-readable instructions for performing robust classification causes the processor to implement: at least one low-dimensional classifier in communication with the receiver, wherein each of the at least one low-dimensional classifiers is associated with a respective input feature from the feature set and provides an output based on the presence of the input feature in the received data; and a weighted adder in communication with the receiver and each of the at least one low-dimensional classifiers, wherein the weighted adder provides a weighted sum of the outputs of the at least one low-dimensional classifier.

In some embodiments of the apparatus, the received data comprises at least one training example. In some embodiments of the apparatus, each of the at least one low-dimensional classifiers is trained using the received at least one training example. In some embodiments of the apparatus, the weighted adder adjusts the weight assigned to the output of each of the at least one low-dimensional classifiers in response to the received at least one training example.

In some embodiments of the apparatus, the received data is selected from the group consisting of vital signs and lab measurements. In some embodiments of the apparatus, the weighted adder adjusts the weights in response to the presence or absence of at least one feature in the received data.

In some embodiments of the apparatus, the output of the weighted adder is a hemodynamic instability score.

In some embodiments of the apparatus, the weighted adder assigns a weight of zero to a classifier whose associated feature is absent from the received data and otherwise assigns a non-zero weight to a classifier whose associated feature is present in the received data.

In some embodiments of the apparatus, at least one of the low-dimensional classifiers is configured to output a zero value when its associated feature is absent from the received data. In some embodiments of the apparatus, the weighted adder adjusts the weight assigned to the output of at least one of the low-dimensional classifiers outputting a non-zero value in response to the output of a zero value by at least one of the low-dimensional classifiers.

According to another aspect of the present disclosure, various embodiments relate to a method for robust classification. The method includes: receiving, via a receiver, data having at least one feature from a feature set; applying at least one low-dimensional classifier to the received data, each of the at least one low-dimensional classifiers being associated with a respective input feature of the feature set, the application of the at least one low-dimensional classifier resulting in an output based on the presence of the input feature in the received data; and outputting a weighted sum, using a weighted adder, based on the outputs of the at least one low-dimensional classifier.

In some embodiments of the method, receiving the data comprises receiving at least one training example. In some embodiments, each of the at least one low-dimensional classifiers is trained using the received at least one training example. In some embodiments, the weight assigned to the output of each of the at least one low-dimensional classifiers is adjusted in response to the received at least one training example.

In some embodiments of the method, the received data is selected from the group consisting of vital signs and lab measurements. In some embodiments, the assigned weights are adjusted in response to the presence or absence of at least one feature in the received data. In certain embodiments, the weighted sum output is a hemodynamic instability score.

In some embodiments of the method, outputting a weighted sum of the classifier outputs comprises assigning a weight of zero to a classifier whose associated feature is absent from the received data and otherwise assigning a non-zero weight to a classifier whose associated feature is present in the received data.

In some embodiments of the method, at least one of the low-dimensional classifiers is configured to output a zero value when its associated feature is absent from the received data.

In some embodiments of the method, the weight assigned to the output of at least one of the low-dimensional classifiers outputting a non-zero value is adjusted in response to the output of a zero value by at least one of the low-dimensional classifiers.

According to yet another aspect of the disclosure, various embodiments relate to a computer readable medium containing computer-executable instructions for performing a method for robust classification. The medium includes computer-executable instructions for receiving, via a receiver, data having at least one feature from a feature set; computer-executable instructions for applying at least one low-dimensional classifier to the received data, each of the at least one low-dimensional classifiers being associated with a respective input feature of the feature set, the application of the at least one low-dimensional classifier resulting in an output based on the presence of the input feature in the received data; and computer-executable instructions for outputting a weighted sum using a weighted adder, based on the outputs of the at least one low dimensional classifier.

In some embodiments of the medium, the instructions for outputting a weighted sum of the classifier outputs comprise instructions for assigning a weight of zero to a classifier whose associated feature is absent from the received data and otherwise assigning a non-zero weight to a classifier whose associated feature is present in the received data.

In some embodiments of the medium, at least one of the low-dimensional classifiers is configured to output a zero value when its associated feature is absent from the received data.

In some embodiments of the medium, the weight assigned to the output of at least one of the low-dimensional classifiers is adjusted in response to the output of a zero value by at least one of the low-dimensional classifiers.

These and other features and advantages, which characterize the present non-limiting embodiments, will be apparent from a reading of the following detailed description and a review of the associated drawings. It is to be understood that both the foregoing general description and the following detailed description are explanatory only and are not restrictive of the non-limiting embodiments as claimed.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. Various embodiments will now be described, by way of example, with reference to the accompanying drawings, in which.

DETAILED DESCRIPTION

Various embodiments are described more fully below with reference to the accompanying drawings, which form a part hereof, and which show specific exemplary embodiments. However, the concepts of the present disclosure may be implemented in many different forms and should not be construed as limited to the embodiments set forth herein; rather, these embodiments are provided as part of a thorough and complete disclosure, to fully convey the scope of the concepts, techniques and implementations of the present disclosure to those skilled in the art. Embodiments may be practiced as methods, systems or apparatus. Accordingly, embodiments may take the form of a hardware implementation, an entirely software implementation or an implementation combining software and hardware aspects. The following detailed description is, therefore, not to be taken in a limiting sense.

Reference in the specification to "one embodiment" or to "an embodiment" means that a particular feature, structure, or characteristic described in connection with the embodiments is included in at least one example implementation or technique in accordance with the present disclosure. The appearances of the phrase "in one embodiment" in various places in the specification are not necessarily all referring to the same embodiment.

Some portions of the description that follow are presented in terms of symbolic representations of operations on non-transient signals stored within a computer memory. These descriptions and representations are used by those skilled in the data processing arts to most effectively convey the substance of their work to others skilled in the art. Such operations typically require physical manipulations of physical quantities. Usually, though not necessarily, these quantities take the form of electrical, magnetic or optical signals capable of being stored, transferred, combined, compared and otherwise manipulated. It is convenient at times, principally for reasons of common usage, to refer to these signals as bits, values, elements, symbols, characters, terms, numbers, or the like. Furthermore, it is also convenient at times, to refer to certain arrangements of steps requiring physical manipulations of physical quantities as modules or code devices, without loss of generality.

However, all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices. Portions of the present disclosure include processes and instructions that may be embodied in software, firmware or hardware, and when embodied in software, may be downloaded to reside on and be operated from different platforms used by a variety of operating systems.

The present disclosure also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each may be coupled to a computer system bus. Furthermore, the computers referred to in the specification may include a single processor or may be architectures employing multiple processor designs for increased computing capability.

The processes and displays presented herein are not inherently related to any particular computer or other apparatus. Various general-purpose systems may also be used with programs in accordance with the teachings herein, or it may prove convenient to construct more specialized apparatus to perform one or more method steps. The structure for a variety of these systems is discussed in the description below. In addition, any particular programming language that is sufficient for achieving the techniques and implementations of the present disclosure may be used. A variety of programming languages may be used to implement the present disclosure as discussed herein.

In addition, the language used in the specification has been principally selected for readability and instructional purposes and may not have been selected to delineate or circumscribe the disclosed subject matter. Accordingly, the present disclosure is intended to be illustrative, and not limiting, of the scope of the concepts discussed herein.

Figure 1:
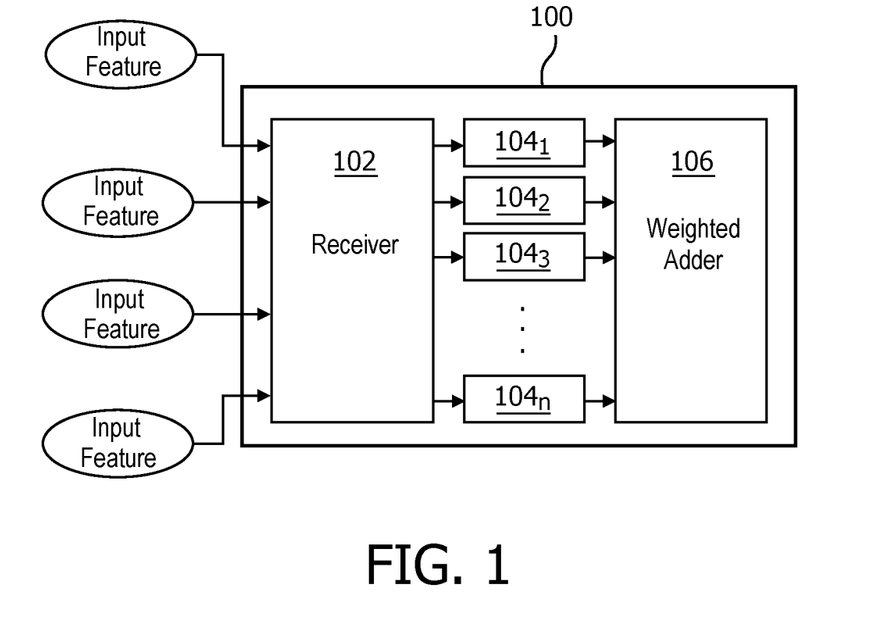
FIG. 1 illustrates a robust classification apparatus in accordance with one embodiment.

FIG. 1 schematically illustrates a robust classifier 100 in accordance with an exemplary embodiment. In this embodiment, the robust classifier 100 may include a receiver 102, at least one low-dimensional classifier device $104_{1, 2, 3 \ldots n}$, and a weighted adder 106. Various embodiments may be used in a variety of applications, namely, any application that relies on data. For example, various embodiments may be used in healthcare, finance, market analysis, sports analysis, retail, etc.

In operation, the receiver element 102 receives at least one input feature from at least one data source (not shown). If the robust classifier 100 is implemented in a healthcare setting, for example, the data sources may be sensor devices for gathering information (i.e., features) from a patent. This information may be related to the patient's heart rate (HR) (in which case the corresponding sensor device would be a heart rate sensor), blood pressure, weight, metabolism, age, etc.

Although four input features are illustrated, it is contemplated that more or less than four input features may be used and the number of input features may depend on the application. The data sources may communicate the features to the receiver 102 via any type of hardwired or wireless connection.

Data from each of the data sources may be associated with at least one feature. Features may be traits, characteristics, or variables that describe the subject (e.g., a patient). Each feature may then be communicated to a designated low-dimensional classifier device 104.

Each classifier device 104 may then output a prediction score, or a zero (0) if any of its dependent features are missing. These classifier devices 104 can be trained independently of one another, or jointly using a multivariate learning technique, such as boosting.

The scores may then be communicated to a weighted adder 106. The weighted adder 106 may also be in communication with the receiver device 102. The weighted adder 106 may assign weights to each feature, and the weights assigned by the adder 106 may depend on the presence or absence of certain features in the input data. The weighted adder 106 may then output the sum of the weighted classifier outputs as a prediction for the model, thereby providing robust data analysis and classification notwithstanding missing or incomplete data.

Various embodiments involve two stages: (1) training; and (2) real-time prediction using the trained model. The training stage can be further broken down into (a) training of the low-dimensional classifiers; and (b) training of the dynamic ensemble model. In various embodiments, these two stages may be performed by the same device while, in other embodiments, a first device may perform the training stage while a second device performs the real-time prediction stage. For example, a training device may process a training set to create the trained model, which may then be distributed among many real-time prediction devices deployed among various locations.

Various embodiments handle missing or incomplete data without data imputation. This makes the features described herein applicable across a wide range of problems. Various embodiments train a set of low-dimensional classifiers and combine them into a powerful ensemble. The weighting of the classifiers in the ensemble is dynamic and varies according to the measured features in the present inputs, which therefore increases robustness and resilience to missing data.

Figure 2:
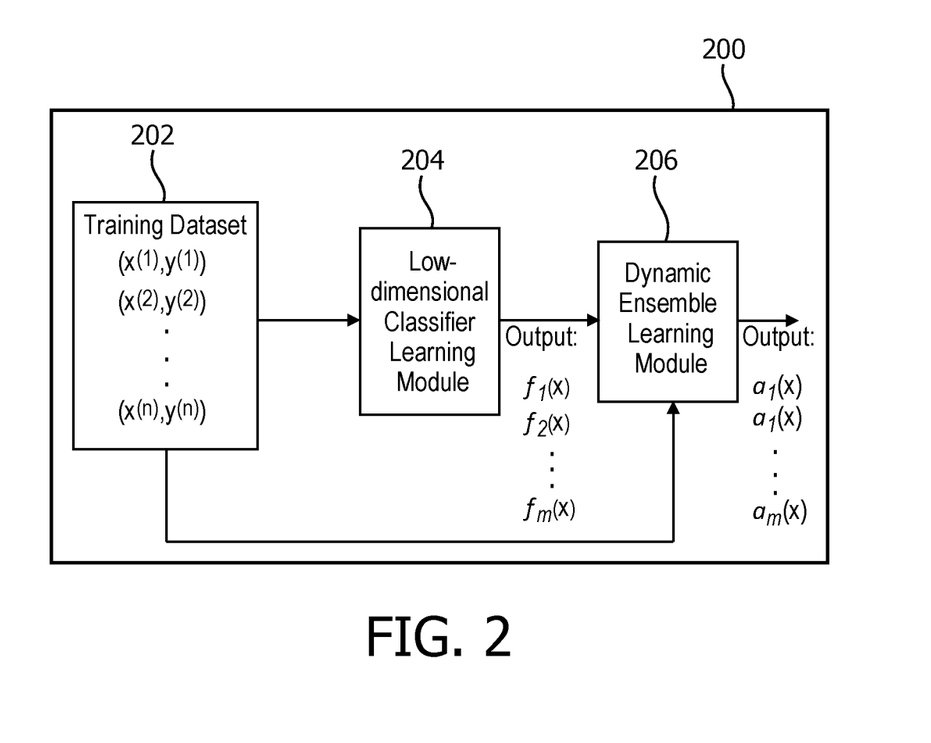
FIG. 2 schematically illustrates a predictive training module that may be used in conjunction with the robust classification apparatus 100 of FIG. 1.

FIG. 2 illustrates a training module 200 in accordance with one embodiment. The training module 200 may be implemented with or otherwise used in conjunction with the robust classification apparatus 100 of FIG. 1. The training stage may receive as input a set of n labelled training examples $((x)^{(1)}, (y)^{(1)}), \ldots, ((x)^{(m)}, (y)^{(m)})$ in a training dataset 202. Each input $x^{(i)}$ is a p-dimensional input pattern, and its $j^{th}$ input element of the $i^{th}$ training example may be denoted by $x_j^{(i)}$; $y^{(i)}$ is the associated categorical label or other output value that was measured or otherwise determined to be correct for the input set of the $i^{th}$ training example. Missing values are allowed, i.e., $x_j^{(i)}$ is assumed to be missing for some features j and training examples i. The goal is to build a model that predicts new output values (consistent with those in the training set, $y^{(i)}$) from new sets of inputs (consistent with those in the training set, $x^{(i)}$).

To accomplish this goal, multiple univariate or low-dimensional classifiers are trained using a machine learning approach such as, for example, logistic or linear regression. The low-dimensional classifier training module(s) 204 each train a set of m low-dimensional classifiers, $f_1(x)$, $f_2$ (x), . . . . $f_m(x)$, where each classifier accepts one or more input features and provides an output. The number of classifiers trained, m, is typically on the order of the number of features in the dataset, p. For example, when each classifier f(x) is a function of only one input feature, then m=p. Each classifier outputs a prediction score, or 0 if any of its dependent features are missing. These classifiers $f_1(x)$, $f_2(x)$, . . . , $f_m(x)$ can be trained independently of one another, or jointly using a multivariate training technique, such as boosting.

Features of the embodiments described herein may be implemented in a variety of applications. Namely, embodiments may be adapted to virtually any type of data-reliant application that may suffer from missing or incomplete data.

In a healthcare setting, data concerning certain patient vital signs and/or lab values may be missing or incomplete due to patient monitoring deficiencies. For example, a patient-monitoring device may malfunction, a caregiver may forget to obtain such information, or acquisition of such information may not be part of the patient's treatment plan. When data concerning certain patient vital signs and/or lab values is present, however, these features can be highly discriminative in predicting aspects of patient state. Therefore, it is desirable to have techniques to utilize sparsely measured or incomplete features (i.e., missing data) in a predictive model.

In one embodiment, for example, the features of the embodiments described herein may be used to predict the hemodynamic instability of a patient. The fundamental purpose of the cardiovascular system is to ensure adequate perfusion and oxygenation of body tissue to maintain normal, healthy tissue and organ function. Under normal circumstances, in a healthy physiological system, there are a number of feedback loops and compensatory mechanisms in place that help to maintain an appropriate blood pressure and cardiac output to enable sufficient perfusion of the end organs.

Among patients who are physiologically fragile, however, like those typically encountered in the intensive care unit (ICU), these mechanisms can become compromised; significant disease processes such as sepsis, hemorrhage, and acute heart failure may result in significant impairment of these control functions to allow hemodynamic deterioration. Thus, in such cases, the ICU clinician is often challenged to optimize hemodynamics by assimilating the myriad ICU data and reacting with appropriate interventions in the form of intravenous fluids, blood products, and pharmacological agents to help the patient maintain adequate cardiac output and perfusion. The early detection of hemodynamic instability episodes and the immediate initiation of appropriate corrective intervention can significantly improve patient outcome.

ICU clinicians are presented with a large number of physiological data consisting of periodic and frequently sampled measurements (e.g. second-by-second, minute-by-minute, 5-minute, or 15-minute, depending on the particular device configuration), such as heart rate and respiratory rate, as well as aperiodic measurements, such as noninvasive blood pressure and laboratory studies. They must acquire, aggregate, and interpret these rich data sources for each patient under their care. The interpretation and reaction to impending hemodynamic instability can be a particularly difficult task in the presence of overwhelming volumes of data, frequent false alarms, and frequently interrupted workflows.

Features of the present application may therefore help clinicians detect hemodynamic deterioration in its early stages or even before onset, thereby enabling them to direct attention to those patients who may benefit from it most. The robust classification apparatus may accomplish this by meaningfully combining data that is available in the current ICU environment. This is an improvement over previous techniques in that it makes use of information that may not be commonly measured, but when measured can be very important. It is important to emphasize that this technique is not meant to replace existing failsafe mechanisms, such as alarms that sound when blood pressure decreases to a critical level (e.g. systolic blood pressure <90 mmHg); rather, it is meant to augment these alarms by drawing attention to precursor conditions that are likely to require interventions, thus giving the clinician more time to take corrective action.

In this embodiment, the output of the robust classification apparatus may be a hemodynamic instability score. This score may be used to accurately predict hemodynamic instability of a patient even though certain information may be missing or incomplete. Although the previous discussion is directed towards hemodynamic instability risk scoring, the features of the present application may be implemented in any other type of application (both inside the area of clinical decision support and out) and, in particular, in applications that may suffer from missing or incomplete data.

Figure 3:
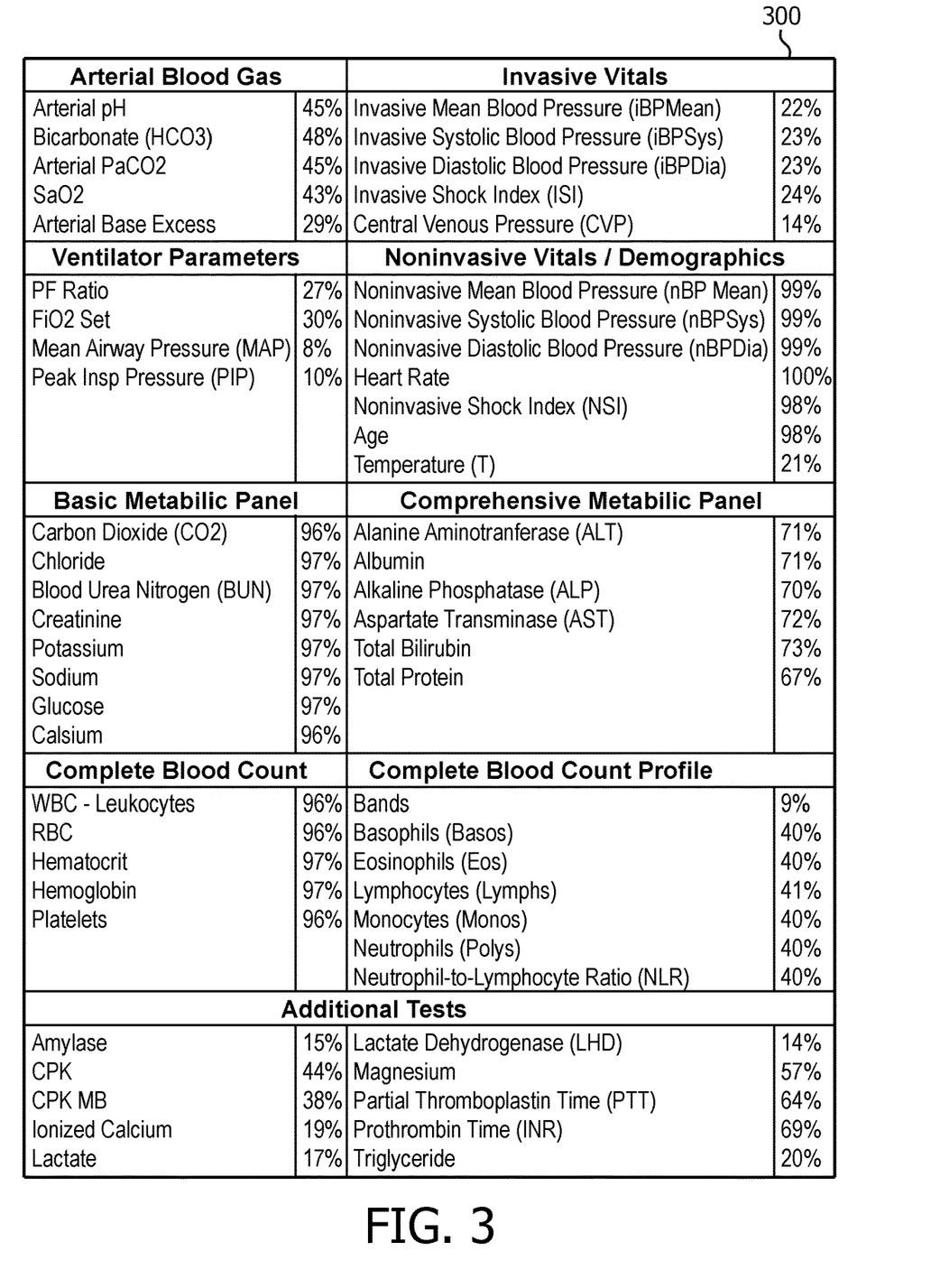
FIG. 3 illustrates a table showing exemplary features that may be considered in calculating a hemodynamic score using the robust classification apparatus 100 of FIG. 1.

FIG. 3, for example, shows a table 300 listing exemplary features that may be used in calculating a hemodynamic risk score and their measurement frequency (i.e., percentage of patients with at least one measurement for that feature). In this case, each input feature $x^{(i)}$ may correspond to a feature listed in table 300 and $y^{(i)}$ is the patient state label (which in this case may be may be a risk score representing the stability of a patient, such as a score from 0 to 1).

Table 300 of FIG. 3 illustrates that data may often be incomplete and that features may not be present or measured in every feature pattern. For example, certain features, such as Lactate and Central Venous Pressure, may each be missing from 80% or more of samples.

Continuing with the illustration in FIG. 2, after the classifiers $f_1(x)$, $f_2(x)$, . . . , $f_m(x)$ are obtained (or trained, e.g., generated from the low-dimensional classifier training module 204), the dynamic ensemble learning module 206 assigns weights to each of the m low-dimensional classifiers to form an ensemble. The weights assigned to each classifier f(x) are dynamic, i.e., a parametric function of the presence or absence of individual measured features in the input. The assigned weighting modulates the strength of each individual classifier's effect on the aggregated risk score.

For example, let $H(x)=f_1(x_1)+f_2(x_2)+f_3(x_3)$ where the three univariate classifiers are approximately linearly dependent such that:

$$\beta_1 f_1(x_1) + \beta_2 f_2(x_2) + \beta_3 f_3(x_3) \approx 0$$

and $\beta_1$, $\beta_2$, and $\beta_3$ are scalars. That is, although the features themselves are not assumed to be dependent, their univariate classifier predictions are assumed to be correlated.

The goal is to faithfully reproduce the predictions of H(x) above in the case of missing data (i.e., if a feature is not present). For example, suppose that a given input pattern is missing a value for $x_1$ ($x_1=\phi$), which causes $f_1(x_1)$ to abstain from providing an output. We can account for $f_1(x_1)$ by reproducing it given $f_2(x_2)$ and $f_3(x_3)$ so that:

$$H(x-(\phi, x_2, x_3)) \approx \left(1 - \frac{\beta_2}{\beta_1}\right) f_2(x_2) + \left(1 - \frac{\beta_3}{\beta_1}\right) f_3(x_3)$$

Similar equations can be derived if $x_2$ or $x_3$ is missing.

The next step is to identify weighting functions $a_1(x), \ldots, a_m(x)$ to form an ensemble classifier $H(x)$:

$$H(x) = a_1(x)f_1(x) + \ldots + a_m(x)f_m(x)$$

The weighting functions $a(x)$ are provided by the dynamic ensemble learning module 206 and their particular values depend on which features are present in the input. That is:

$$a_i = s_{i0} + s_{i1}m(x_1) + \ldots + s_{ip}m(x_p)$$

where $s_{ij}$ are coefficients and $m(x_j)$ is an indicator mask that results in a binary vector $m = (m_1, m_2, \ldots, m_p)$, where $m_j = 0$ when the jth feature is missing, or 1 when the jth feature is measured. Combining the above equations, the ensemble classifier can be written as:

$$H(x) = \Sigma \text{hd } i=1^m s_{i0}f_i(x) + \Sigma_{i=1}^m \Sigma_{j=1}^p s_{ij} f_i(x) m(x_j)$$

From this equation, the classifier $H(x)$ is linear in the coefficients, $s_{ij}$, $i=1, \ldots, m$, $j=0, 1, \ldots, p$, so these coefficients may be learned using standard linear classification techniques, such as logistic regression to predict the labels on the training set. Specifically, to predict $y^{(1)}$, $y^{(2)}, \ldots, y^{(n)}$ from $H(x^{(1)})$, $H(x^{(2)})$, ... . $H(x^{(n)})$.

The final predictive model is defined by $H(x)$, which is constituted from the m low-dimensional classifiers $f_1(x)$, $f_2(x), \ldots, f_m(x)$, as well as the weighting functions $a_1(x), \ldots, a_n(x)$, which are parameterized by the coefficients $s_{ij}$, $i=1, \ldots, m$, $j=0, 1, \ldots, p$. In the hemodynamic scoring application, for example, the coefficients $s_{ij}$, $i=1, \ldots, m$, $j=0, \ldots, p$ may be learned in a secondary offline stage on training data prior to deployment.

Thus, each classifier's weight is dynamic and depends on the measurement pattern of the features. This allows the final classifier 100 to accommodate missing data by adjusting the strength of other classifiers (i.e., by adjusting the weights) in the ensemble based on the presence and absence of certain features.

Figure 4:
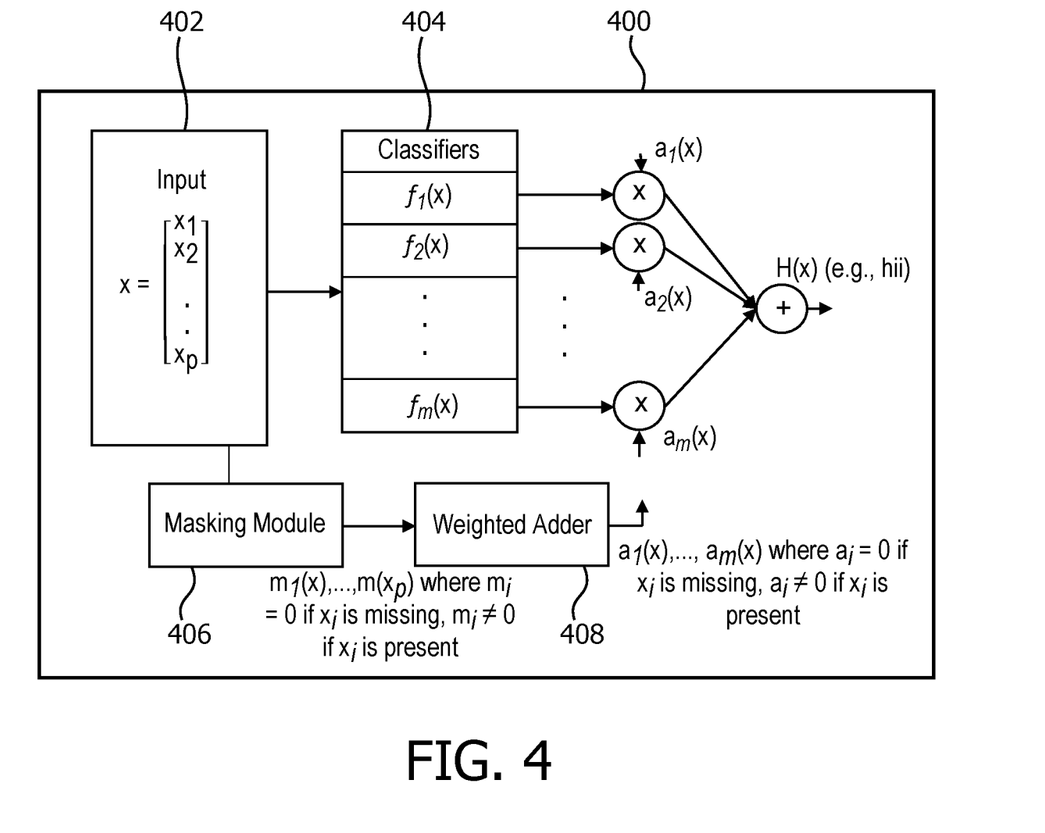
FIG. 4 schematically illustrates a real-time prediction module that may be used in conjunction with the robust classification apparatus 100 of FIG. 1.

Once the classifier has been constructed, it is applied in real-time to perform classification on sparse or incomplete data sets. FIG. 4 illustrates one embodiment of a real-time prediction module 400. The real-time prediction module 400 may be implemented with or otherwise used in conjunction with the robust classification apparatus 100 of FIG. 1. Once the predictive model has been trained, the real-time prediction module 400 can evaluate new inputs which may include missing data. In this stage, a predictive score is assigned to a new input x by computing the model prediction $H(x)$.

The input x 402 may include a series of p features $x_1$, $x_2, \ldots, x_p$. If the robust classification apparatus is used in calculating a patient's hemodynamic score, as discussed above, these features may include any of the features listed in table 300 of FIG. 3. Next, each low-dimensional classifier $f_1(x), f_2(x), \ldots, f_n(x)$ 404 is applied to the input x, wherein each classifier $f_1(x), f_2(x), \ldots, f_n(x)$ 404 is associated with an input feature $x_1, x_2, \ldots, x_p$. In embodiments wherein one or more classifiers 404 may be multi-variate (e.g. low-dimensional but not univariate), such classifiers may be associated with more than one of the input features.

The masking module 406 may then determine the appropriate masks $m(x_1), \ldots, m(x_p)$ for each of the p features. Note that $m(x_j)=0$ if the jth feature is missing, and $m(x_j)=1$ if the jth feature is present. As mentioned previously, the weighted adder 408 can assign weights by using the equation:

$$a_i = s_{i0} + s_{i1}m(x_1) + \ldots + s_{ip}m(x_p)$$

The weighted adder 408 applies weights $a_1(x), \ldots, a_m(x)$ to the output of the classifiers $f_1(x), f_2(x), \ldots f_m(x)$ to output a single score $H(x)$. In the hemodynamic score embodiment, a single hemodynamic instability indicator (hii) risk score may be represented by:

$$hii(x) = \Sigma_{i=1}^P a_i(x) f_i(x_i)$$

As this is a weighted average of the constituent univariate classifiers for hii, the weighting may depend on the measurement pattern of the input (e.g., which features of FIG. 3 are present/absent from the input x). Certain features may be weighed more or less strongly based on which feature(s) are missing.

The weighted adder 408 may adjust a feature's weight to essentially replace a missing feature if the "replacement" feature is often measured when the other feature is not measured. As an example in the hemodynamic instability scoring application, Hemoglobin and Hematocrit are highly correlated and there are few circumstances in which one is measured but not the other—therefore, they have little value in replacing each other. Thus, the weighted adder 408 may be biased to select "replacement" features that are either measured very frequently or measured exclusively of the missing feature.

There are a number of relationships of this kind that may develop in the hemodynamic instability scoring application. For example, with reference to FIG. 3, Lactate is measured in approximately only 17% of patients. In these cases, the dominant feature that is adjusted to account for the missing Lactate feature is Arterial $PaCO_2$ (which is measured in 45% of patients). Arterial $PaCO_2$ is weighted strongly because both Lactate and Arterial $PaCO_2$ are related to anaerobic respiration.

As another example, bicarbonate ($HCO_3$) measurements are present in just 48% of examples. In these cases, missing bicarbonate measures are accounted for by adjusting the weight of the carbon dioxide predictor (which is available for 96% of examples when bicarbonate is missing). Carbon dioxide is weighted accordingly because a majority of carbon dioxide in the blood exists in the form of bicarbonate.

The outputted hii score may be on a non-normalized scale in which large positive values may indicate high risks of hemodynamic instability and large negative values may indicate low risks of hemodynamic instability. To produce a more intuitive, user-friendly score for clinicians or other interested parties, the score may be normalized by, for example, passing it through a sigmoid function, e.g.:

$$HII(x) = \frac{1}{1 + \exp(-hii(x))}$$

This produces a normalized score $HII(x)$ in the range $[0,1]$, wherein values close to 1 may indicate a high risk of hemodynamic instability and values closer to 0 may indicate a lower risk of hemodynamic instability. This score may be presented to a clinician or other type of medical personnel via a graphical display. Similarly, HII scores may be associated with colors to further emphasize the level of risk (e.g., green=low risk, yellow=medium risk, red=high risk, etc.).

Figure 5:
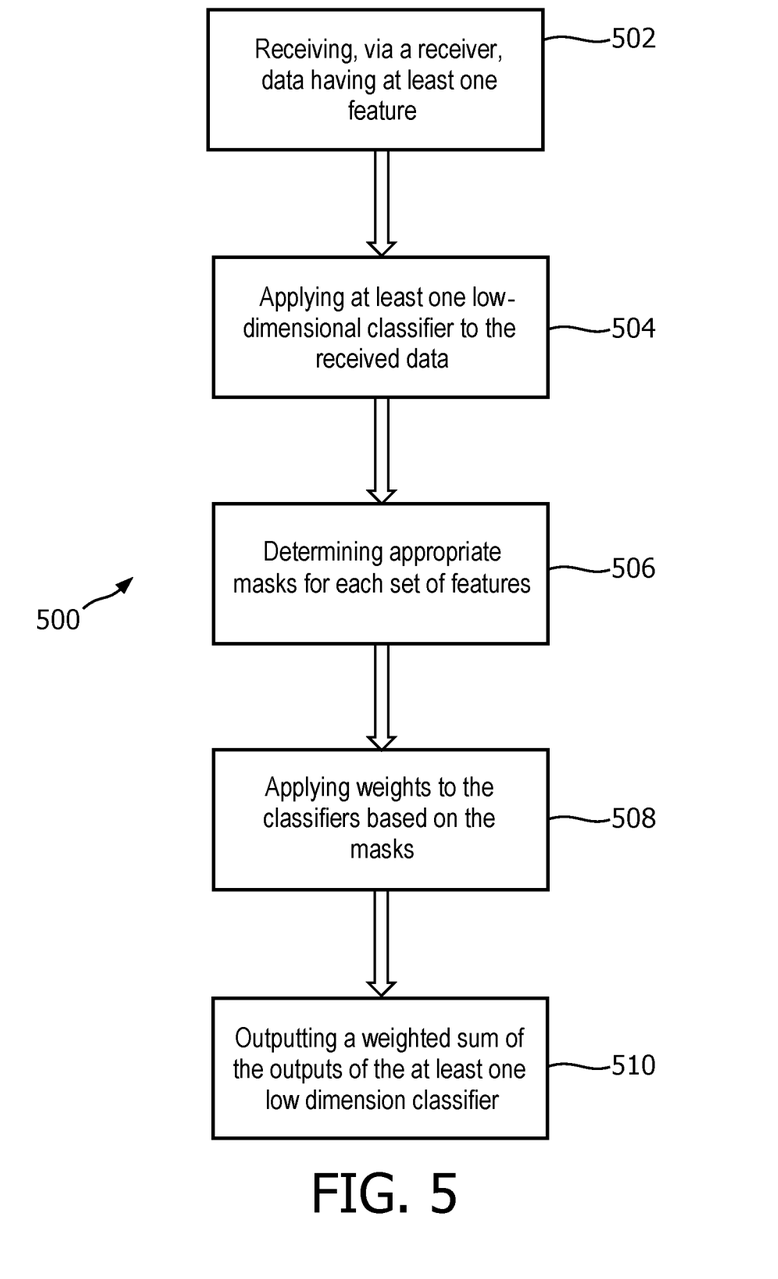
FIG. 5 depicts a flowchart of a method for robust classification in accordance with one embodiment.

FIG. 5 depicts a flowchart of a method 500 for robust classification in accordance with one embodiment. Step 502 involves receiving, via a receiver, data having at least one feature. The receiver may receive the data by any hardwired or wireless connection. This data may relate to a patient's health, for example, and may be entered by medical personnel and/or received from health monitoring systems or devices.

In the predictive training stage, the received data comprises at least one training example. That is, at least one low-dimensional classifier is trained using the training example.

Step 504 involves applying at least one low-dimensional classifier to the received data. This results in an output based on the received data, wherein each of the low-dimensional classifiers are associated with one of the features in the received data.

Step 506 involves determining appropriate masks for each set of features. As stated previously, $m(x_j)=0$ if the jth feature is missing, and $m(x_j)=1$ if the jth feature is present. This step may be performed by the masking module 406.

Step 508 involves applying weights to the classifiers based on the masks. These weights depend on the masks, and namely, which features in the input were measured. This step may be performed by the weighted adder 408.

Step 510 involves outputting a weighted sum of the outputs of the at least one classifier. As stated previously, the weighted sum is dependent on, in part, which features are absent and which are present. The weight assigned to the output of each classifier is also dependent on the training example. In the hemodynamic instability score application, this output may be a hemodynamic risk score indicating whether a patient is at risk of hemodynamic instability.

Figure 6:
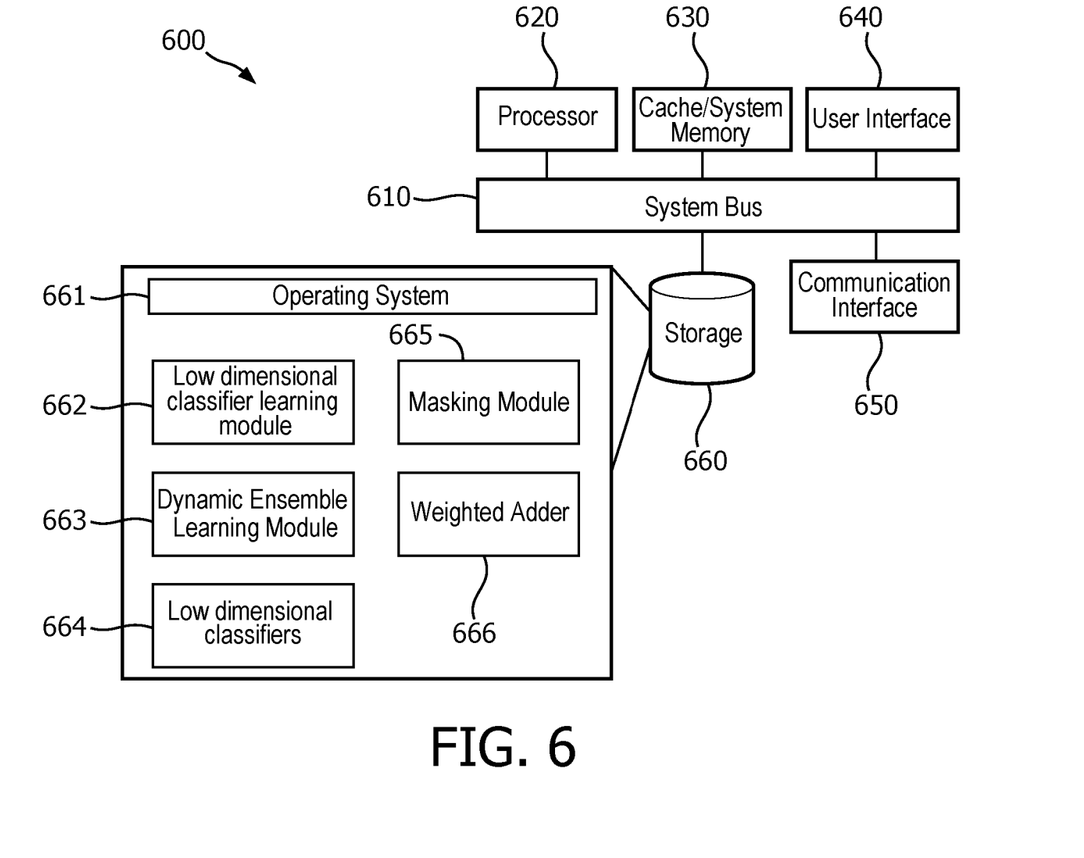
FIG. 6 presents a system for robust classification of data sets in accordance with one embodiment.

FIG. 6 illustrates an example of hardware system 600 for implementing various devices that may participate in the various systems described herein. The hardware 600 may implement a user mobile device or a supporter mobile device. As shown in FIG. 6, the hardware 600 includes one or more system buses 610 that connect a processor 620, cache/system memory 630, a user interface 640, a communication interface 650, and storage 660. It will be understood that FIG. 6 is merely exemplary and constitutes, in some respects, an abstraction and that the actual organization of the components of the hardware 600 may vary and be more complex than illustrated.

The processor 620 may be any hardware device capable of executing instructions stored in memory 630 or storage 660 or otherwise processing data. As such, the processor 620 may include a microprocessor, a field programmable gate array (FPGA), application-specific integrated circuit (ASIC), or other similar devices. In some embodiments, such as those relying on one or more ASICs, the functionality described as being provided in part via software may instead be hardwired into the operation of the ASICs and, as such, the associated software may be omitted.

The cache/system memory 630 may include various memories such as, for example, L1, L2, or L3 cache or system memory. As such, the memory 630 may include static random access memory (SRAM), dynamic RAM (DRAM), flash memory, read only memory (ROM), or other similar memory devices.

The user interface 640 may include one or more devices for enabling communication with a user such as an administrator. For example, the user interface 640 may include a display, a mouse, a keyboard, a touchscreen, buttons, camera, microphone, vibrator, haptic engine, etc. In some embodiments, the user interface 640 may include a command line interface or graphical user interface that may be presented to a remote terminal via the communication interface 650.

The communication interface 650 may include one or more devices for enabling communication with other hardware devices. For example, the communication interface 650 may include a network interface card (NIC) configured to communicate according to the Ethernet protocol. Additionally, the communication interface 650 may implement a TCP/IP stack for communication according to the TCP/IP protocols. Various alternative or additional hardware or configurations for the communication interface 650 will be apparent. In some embodiments, the communication interface 650 may include an NFC, Bluetooth, or other short range wireless interface. Various alternative or additional hardware or configurations for the communication interface 650 will be apparent.

The storage 660 may include one or more machine-readable storage media such as read-only memory (ROM), random-access memory (RAM), magnetic disk storage media, optical storage media, flash-memory devices, or similar storage media. In various embodiments, the storage 660 may store instructions for execution by the processor 620 or data upon with the processor 620 may operate. For example, the storage 660 may store an operating system 661 for controlling various basic operations of the hardware 600.

The operating system 661 may include the various components described previously. These components may be the low-dimensional classifier module 662 for example, which may be similar to the low-dimensional classifier learning module 204 of FIG. 2, for example. These components may train a set of m low-dimensional classifiers, $f_1(x)$, $f_2(x)$, ..., $f_m(x)$, where each classifier accepts one or more input features and provides an output.

Another component of the operating system 661 may be the dynamic ensemble learning module 663. The dynamic ensemble learning module 663 of FIG. 6 may be similar to the dynamic ensemble learning module 206 of FIG. 2, for example. The dynamic ensemble learning module 663 may assign weights to each of the m low-dimensional classifiers to form an ensemble. As stated previously, the weights assigned to each classifier f(x) are dynamic and may modulate the strength of each individual classifier's effect on the aggregated risk score.

The low-dimensional classifier(s) 664 may be similar to the low-dimensional classifiers 404 of FIG. 4, for example. Each classifier 664 $f_1(x), f_2(x), \ldots, f_m(x)$ is associated with an input feature $x_1, x_2, \ldots, x_p$. In embodiments wherein one or more classifiers 664 may be multi-variate (e.g. low-dimensional but not univariate), such classifiers may be associated with more than one of the input features.

The masking module 665 may be similar to the masking module 406 of FIG. 4, for example. As stated previously, the masking module 665 may determine the appropriate masks $m(x_1), \ldots, m(x_p)$ for each of the p features. Note that $m(x_j)=0$ if the jth feature is missing, and $m(x_j)=1$ if the jth feature is present.

The weighted adder 666 may be similar to the weighted adder 408 of FIG. 4, for example. As stated previously, the weighted adder 666 applies weights $a_1(x), \ldots, a_m(x)$ to the output of the classifiers $f_1(x), f_2(x), \ldots, f_m(x)$ to output a single score H(x). This is a weighted average of the constituent univariate classifiers, and the weighting may depend on the measurement pattern of the input. Certain features may be weighed more or less strongly based on which feature(s) are missing.

While several embodiments have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, e.g., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, e.g., the inclusion of at least one, but also including more than one, of a number or list of elements, and, optionally, additional unlisted items. Only terms clearly indicated to the contrary, such as "only one of" or "exactly one of," or, when used in the claims, "consisting of" will refer to the inclusion of exactly one element of a number or list of elements. In general, the term "or" as used herein shall only be interpreted as indicating exclusive alternatives (e.g. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, e.g., to mean including but not limited to.

Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. An apparatus for robust classification, the apparatus comprising:
    a receiver receiving data, the received data having at least one feature from a feature set;
    a memory configured to store computer-readable instructions for performing robust classification notwithstanding at least one missing feature from the feature set; and
    a processor in communication with the memory and receiver, wherein execution of the computer-readable instructions for performing robust classification causes the processor to implement:
        at least one trained low-dimensional classifier in communication with the receiver, wherein each of the at least one low-dimensional classifiers is associated with a respective input feature from the feature set and provides an output based on the presence of the input feature in the received data; and
        a weighted adder in communication with the receiver and each of the at least one trained low-dimensional classifiers, wherein:
            the weighted adder assigns weights to each of the at least one trained low-dimensional classifier and provides a weighted sum of the outputs of the at least one low-dimensional classifier and the assigned weights, and
            the weighted adder assigns a weight of zero to a classifier whose associated feature is absent from the received data and otherwise assigns a non-zero weight to a classifier whose associated feature is present in the received data.

2. The apparatus as defined in claim 1, wherein the received data comprises at least one training example.

3. The apparatus as defined in claim 2, wherein each of the at least one low-dimensional classifiers is trained using the received at least one training example.

4. The apparatus as defined in claim 3, wherein the weighted adder adjusts the weight assigned to the each of the at least one low-dimensional classifiers in response to the received at least one training example.

5. The apparatus as defined in claim 1, wherein the output of the weighted adder is a hemodynamic instability score.

6. The apparatus as defined in claim 1, wherein at least one of the trained low-dimensional classifiers is configured to output a zero value when its associated feature is absent from the received data.

7. The apparatus as defined in claim 6, wherein the weighted adder adjusts the weight assigned to the output of at least one of the trained low-dimensional classifiers outputting a non-zero value in response to the output of a zero value by at least one of the low-dimensional classifiers.

8. A method performed by a processor executing instructions stored on a memory for performing robust classification notwithstanding at least one missing feature from a feature set, the method comprising:
receiving, via a receiver, data having at least one feature from a feature set;
applying at least one trained low-dimensional classifier to the received data, each of the at least one trained low-dimensional classifiers being associated with a respective input feature of the feature set, the application of the at least one low-dimensional classifier resulting in an output based on the presence of the input feature in the received data; and
assigning, using a weighted adder, weights for each of the at least one trained low-dimensional classifiers and outputting a weighted sum, using the weighted adder, based on the outputs of the at least one trained low-dimensional classifier and the assigned weights, wherein the outputting further comprises:
assigning a weight of zero to a classifier whose associated feature is absent from the received data and otherwise assigning a non-zero weight to a classifier whose associated feature is present in the received data.

9. The method as defined in claim 8, wherein receiving the data comprises receiving at least one training example.

10. The method as defined in claim 9, wherein each of the at least one trained low-dimensional classifiers is trained using the received at least one training example.

11. The method as defined in claim 10, wherein the weight assigned to of the at least one low-dimensional classifiers is adjusted in response to the received at least one training example.

12. The method as defined in claim 8, wherein the weighted sum outputted is a hemodynamic instability score.

13. The method as defined in claim 8, wherein at least one of the trained low-dimensional classifiers is configured to output a zero value when its associated feature is absent from the received data.

14. The method as defined in claim 13, wherein the weight assigned to the output of at least one of the low-dimensional classifiers outputting a nonzero value is adjusted in response to the output of a zero value by at least one of the trained low-dimensional classifiers.

15. A non-transitory computer readable medium containing computer-executable instructions for execution by a processor for performing a method for robust classification on a feature set notwithstanding at least one missing feature, the medium comprising:
computer-executable instructions for receiving, via a receiver, data having at least one feature from a feature set, wherein the received data comprises at least one training example;
computer-executable instructions for applying at least one trained low-dimensional classifier to the received data, wherein:
each of the at least one trained low-dimensional classifiers is associated with a respective input feature of the feature set,
the application of the at least one trained low-dimensional classifier results in an output based on the presence of the input feature in the received data, and
each of the at least one trained low-dimensional classifiers is trained using the received at least one training example;
computer-executable instructions for assigning, using a weighted adder, weights for each of the at least one trained low-dimensional classifiers and outputting a weighted sum using a-the weighted adder, based on the outputs of the at least one trained low dimensional classifier and the assigned weights, wherein the weighted adder adjusts the weight assigned to each of the at least one trained low-dimensional classifiers in response to the received at least one training example.

16. The medium as defined in claim 15, wherein the instructions for outputting a weighted sum of the classifier outputs and the assigned weights comprise instructions for assigning a weight of zero to a classifier whose associated feature is absent from the received data and otherwise assigning a non-zero weight to a classifier whose associated feature is present in the received data.

17. The medium as defined in claim 15, wherein at least one of the trained low-dimensional classifiers is configured to output a zero value when its associated feature is absent from the received data.

18. The medium as defined in claim 15, wherein the weight assigned to the at least one of the trained low-dimensional classifiers is adjusted in response to the output of a zero value by at least one of the trained low-dimensional classifiers.

19. The medium as defined in claim 15, wherein the output of the weighted adder is a hemodynamic instability score.

20. The medium as defined in claim 17, wherein the weighted adder adjusts the weight assigned to the output of at least one of the trained low-dimensional classifiers outputting a non-zero value in response to the output of a zero value by at least one of the low-dimensional classifiers.

* * * * *